(12) United States Patent
Hosoda et al.

(10) Patent No.: US 11,268,168 B2
(45) Date of Patent: Mar. 8, 2022

(54) ARTIFACTLESS SUPERELASTIC ALLOY

(71) Applicants: TOKYO INSTITUTE OF TECHNOLOGY, Tokyo (JP); TANAKA KIKINZOKU KOGYO K.K., Tokyo (JP)

(72) Inventors: Hideki Hosoda, Tokyo (JP); Akira Umise, Tokyo (JP); Kenji Goto, Isehara (JP)

(73) Assignees: TOKYO INSTITUTE OF TECHNOLOGY, Tokyo (JP); TANAKA KIKINZOKU KOGYO K.K., Tokyo (JP)

( * ) Notice: Subject to any disclaimer, the term of this patent is extended or adjusted under 35 U.S.C. 154(b) by 9 days.

(21) Appl. No.: 16/641,146

(22) PCT Filed: Aug. 9, 2018

(86) PCT No.: PCT/JP2018/029910
§ 371 (c)(1),
(2) Date: Feb. 21, 2020

(87) PCT Pub. No.: WO2019/039298
PCT Pub. Date: Feb. 28, 2019

(65) Prior Publication Data
US 2020/0190628 A1  Jun. 18, 2020

(30) Foreign Application Priority Data

Aug. 22, 2017 (JP) .............................. JP2017-159554

(51) Int. Cl.
| | |
|---|---|
| *C22C 5/02* | (2006.01) |
| *B21D 22/02* | (2006.01) |
| *B22D 7/00* | (2006.01) |
| *C22C 1/02* | (2006.01) |
| *C22F 1/14* | (2006.01) |

(52) U.S. Cl.
CPC .............. *C22C 5/02* (2013.01); *B21D 22/022* (2013.01); *B22D 7/005* (2013.01); *C22C 1/02* (2013.01); *C22F 1/14* (2013.01)

(58) Field of Classification Search
None
See application file for complete search history.

(56) References Cited

U.S. PATENT DOCUMENTS

| | | | |
|---|---|---|---|
| 2012/0035632 | A1 | 2/2012 | Hamada et al. |
| 2016/0362772 | A1 | 12/2016 | Hosada et al. |
| 2016/0367729 | A1 | 12/2016 | Shima et al. |

FOREIGN PATENT DOCUMENTS

| | | | |
|---|---|---|---|
| CN | 101565783 | * | 5/2009 |
| JP | H02-185936 | A | 7/1990 |
| JP | 2014-084485 | A | 5/2014 |
| JP | 2015-007277 | A | 1/2015 |
| JP | 2015-048485 | A | 3/2015 |
| WO | WO-2010/084948 | A1 | 7/2010 |

OTHER PUBLICATIONS

English language machine translation of CN101565783 to Xuejun et al. Generated Apr. 26, 2021. (Year: 2021).*
International Searching Authority, "International Search Report," issued in connection with International Patent Application No. PCT/JP2018/029910, dated Nov. 6, 2018.
International Searching Authority, "Written Opinion," issued in connection with International Patent Application No. PCT/JP2018/029910, dated Nov. 6, 2018.
Battezzati et al: "A shape memory gold alloy processed by rapid solidification", Journal of Alloys and Compounds, Elsevier Sequoia, Lausanne, CH; vol. 434-435; Mar. 29, 2007; pp. 264-267.
Extended European Search Report dated Apr. 14, 2021 for corresponding European Patent Application No. 18847810.1.
Umise Akira et al: "Martensitic Transformation and Mechanical Properties of AuCuAl-Based Biomedical Shape Memory Alloys Containing Various Quaternary Elements"; Journal of the Japan Institute of Metals and Materials; vol. 80, No. 1; Jan. 1, 2016; pp. 71-76.

* cited by examiner

*Primary Examiner* — Brian D Walck
(74) *Attorney, Agent, or Firm* — Foley & Lardner LLP

(57) ABSTRACT

The present invention provides an artifactless superelastic alloy including a Au—Cu—Al alloy, the superelastic alloy containing Cu in an amount of 20 atom % or more and 40 atom % or less, Al in an amount of 15 atom % or more and 25 atom % or less, and Au as a balance, the superelastic alloy having a bulk magnetic susceptibility of −24 ppm or more and 6 ppm or less. The Ni-free superelastic alloy of the present invention is capable of exhibiting superelasticity in a normal temperature range, and hardly generated artifacts in a magnetic field environment. The alloy can be produced by setting a casting time in a melting and casting step to a fixed time, and hot-pressing an alloy after casting to make material structures homogeneous.

6 Claims, No Drawings

ARTIFACTLESS SUPERELASTIC ALLOY

CROSS-REFERENCE TO RELATED APPLICATIONS

The present application claims priority under 37 U.S.C. § 371 to International Patent Application No. PCT/JP2018/029910, filed Aug. 9, 2018, which claims priority to and the benefit of Japanese Patent Application No. 2017-159554, filed on Aug. 22, 2017. The contents of these applications are hereby incorporated by reference in their entireties.

TECHNICAL FIELD

The present invention relates to a superelastic alloy suitable as a medical material, and particularly to a superelastic alloy which is free from Ni and capable of exhibiting superelasticity in a normal temperature range, and hardly generates artifacts in a magnetic field environment.

BACKGROUND ART

Superelastic alloys are expected to be applied to medical fields in which medical devices such as catheters, stents and embolization coils are used. The superelastic alloy is a metallic material having a very wide elastic range at a temperature equal to or higher than the transformation temperature, and has a property of recovering an original shape even when considerably deformed. The superelastic alloy, which has a transformation temperature in the vicinity of a normal temperature range, can exhibit superelasticity at the human body temperature, and therefore may be applicable to medical devices.

Superelastic alloys best known heretofore in terms of their properties are alloys based on Ni—Ti-based shape memory alloys. However, the Ni—Ti-based alloys are materials lacking in biocompatibility that is the most important property in medical fields because the alloys contain Ni which is a cause of metal allergy.

Thus, alloy materials which can exhibit superelasticity while being free from Ni have been developed. The present applicant discloses superelastic alloys obtained by adding Co, and adding Mo or Nb to a Au—Ti-based shape memory alloy (Patent Document 1), a superelastic alloy obtained by adding Fe or Co to a Au—Cu—Al-based shape memory alloy (Patent Document 2), and so on.

RELATED ART DOCUMENT

Patent Documents

Patent Document 1: JP 2014-84485 A
Patent Document 2: JP 2015-48485 A

SUMMARY OF THE INVENTION

Problems to be Solved by the Invention

Various superelastic alloys as described above can exhibit superelasticity while being free from Ni. In particular, the above-described alloys have Au as a constituent element, and Au has an advantage of being excellent in biocompatibility. The superelastic alloys are suitable for medical devices because the alloys contain a heavy metal, Au, and have a favorable X-ray-imaging property.

However, in view of advancement of treatment and diagnosis methods in medical front, it is hard to say that the above-described superelastic alloys have novel required properties which are being considered important as medical materials. The novel required properties include magnetic properties.

In medical front in recent years, treatments and operations using magnetic resonance imaging diagnostic processors (MRI) have been extensively carried out, and impacts on constituent materials of medical devices in magnetic field environments have become a concern. Problems caused by the impacts include artifacts (false images) of MRI. The artifact is a phenomenon in which a metal is magnetized in a magnetic field, so that MRI images in regions peripheral to the metal are distorted. Generation of artifacts hampers accurate operations and diagnoses. The superelastic alloys for medical use may be unable to suppress artifacts.

The present invention was made against the above-described circumstances, and discloses a superelastic alloy which is free from Ni and capable of exhibiting superelasticity in a normal temperature range, and hardly generates artifacts in a magnetic field environment. Further, the present invention provides an alloy material having higher compatibility than before with respect to use in medical fields.

Means for Solving the Problems

The above-described problems can be solved by attainment of both exhibition of superelasticity and an artifactless property, which is not necessarily easy because these phenomena are different in principle.

A principle of superelasticity is based on a phase transition phenomenon resulting from martensitic transformation of a shape memory alloy, and related to a crystal structure of the alloy. The superelasticity is obtained by employing a constituent element allowing a transformation temperature to be intentionally reduced to a normal temperature range while consideration is given to a crystal structure of the alloy.

On the other hand, the artifact is a phenomenon resulting from magnetization of a metal in a magnetic field, and is therefore related to a magnetic susceptibility (bulk magnetic susceptibility) of the metal. It is to be noted that regarding the problem of artifacts, mere reduction of the magnetic susceptibility is not sufficient, and a certain criterion is set. According to the present inventors, the criterion means that the magnetic susceptibility of the metal is close to a magnetic susceptibility of a tissue of a living body. The magnetic susceptibility of a tissue of a living body is ascribed to water which is a main component of the tissue. Water has a magnetic susceptibility of −9 ppm ($-9\times10^{-6}$), and is slightly diamagnetic. An artifactless material should have a magnetic susceptibility close to the magnetic susceptibility of water. Here, the present inventors set the criteria of the magnetic susceptibility to the magnetic susceptibility of water (−9 ppm)±15 ppm (−24 ppm or more and 6 ppm or less).

While considering the above-described matters, the present inventors paid attention to a Au—Cu—Al alloy as an alloy system capable of attaining exhibition of superelasticity and an artifactless property. As described in Patent Document 2 above, the Au—Cu—Al alloy is a material known as a shape memory alloy, and hence an alloy which likely exhibits superelasticity. Further, the Au—Cu—Al alloy is free from Ni, so that the problem of biocompatibility can be solved.

The Au—Cu—Al also has an advantage stemming from presence of Au. As described above, Au has an X-ray-imaging property as well as biocompatibility, and is therefore suitable as a medical material. Au has an important advantage for suppression of artifacts which is a challenge of the present invention. That is, Au is a diamagnetic metal having a magnetic susceptibility of −34 ppm. As described above, it is preferable that a range close to the magnetic susceptibility (−9 ppm±15 ppm) is set as a criterion of the artifactless material. Au is a metal having a magnetic susceptibility close to the criterion, and hence a metal which is called an origination point for achieving an object of the present invention.

Here, the magnetic susceptibility of the alloy material can be adjusted according to a magnetic property and a composition of a metal to be alloyed. As described above, the magnetic susceptibility of Au is −34 ppm, and can be made close to the criterion value in the present invention (−9 ppm±15 ppm) by slightly shifting the magnetic susceptibility to a positive side. In this respect, in the Au—Cu—Al alloy of the present invention, Al is a paramagnetic metal (magnetic susceptibility: 16 ppm), has a slightly more positive magnetic susceptibility, and thus contributes to adjustment of the alloy magnetic susceptibility by alloying Au. On the other hand, Cu is a diamagnetic metal (magnetic susceptibility: −9 ppm), and therefore has less impacts on the alloy susceptibility as compared to Al. According to the present inventors, it may be possible to form an alloy having a magnetic susceptibility within the above-described criterion by appropriately alloying Au with Al and Cu.

The present inventors extensively conducted studies on the basis of the above considerations, and found an alloy material for a Au—Cu—Al alloy, which has a composition in an appropriate range, and a transformation temperature enabling exhibition of superelasticity in a normal temperature range and which exhibits such a magnetic susceptibility that the alloy material can be considered artifactless, thus arriving at the present invention.

Thus, the present invention provides a superelastic alloy including a Au—Cu—Al alloy, the superelastic alloy containing Cu in an amount of 20 atom % or more and 40 atom % or less, Al in an amount of 15 atom % or more and 25 atom % or less, and Au as a balance, the superelastic alloy having a bulk magnetic susceptibility of −24 ppm or more and 6 ppm or less.

Hereinafter, the present invention will be described in more detail. The artifactless superelastic alloy including an Au—Cu—Al alloy of the present invention is one having Cu and Al added within a suitable range while containing Au as a main constituent element. Hereinafter, constituent metals of the alloy will be described. Hereinafter, "%" indicating an alloy composition means "atom %". The "magnetic susceptibility" means a bulk magnetic susceptibility.

In the Au—Cu—Al alloy of the present invention, an added amount of Cu is 20% or more and 40% or less. Cu is a metal which is mainly involved in exhibition of superelasticity. When a Cu content is less than 20%, superelasticity is not exhibited. When the Cu content is more than 40%, the transformation temperature increases, so that at normal temperature, only a shape memory effect is exhibited, and superelasticity is not exhibited. The magnetic susceptibility may exceed 6 ppm. The Cu content is more preferably 25% or more and 35% or less.

An added amount of Al is 15% or more and 25% or less. In the present invention, Al is also an important constituent metal, is involved in exhibition of superelasticity, and has a relatively high magnetic susceptibility adjustment effect. In addition, Al affects processability of an alloy. When an Al content is less than 15%, it is difficult to exhibit superelasticity at normal temperature, and the magnetic susceptibility adjustment effect is reduced. When the Al content is more than 25%, the transformation temperature excessively decreases, and processability is deteriorated. The Al content is more preferably 18% or more and 25% or less.

A balance based on the added amounts of Cu and Al above is set to a Au content. A Au concentration is preferably 40% or more and 57% or less.

Basically, the superelastic alloy of the present invention can be produced by a melting and casting method. In a basic step, raw materials of the metals are melted to generate a molten metal, and the molten metal is cast to produce a Au—Cu—Al alloy ingot.

In the present invention, it is necessary to simultaneously achieve needs for both a superelastic property and a magnetic property. For making these properties suitable simultaneously, it is necessary to enhance structural homogeneity of the alloy material. Here, for securing homogeneity, a method for producing a superelastic alloy of the present invention includes a melting and casting step including casting a molten metal at a high cooling rate, and a step of hot-pressing a Au—Cu—Al alloy ingot after melting and casting. Thus, the method for producing a superelastic alloy of the present invention includes a step of melting and casting a Au—Cu—Al alloy having the above-described composition, the melting and casting step including producing the Au—Cu—Al alloy with a molten metal solidification time set to 6.0 sec or less, and a hot-pressing step of hot-pressing the Au—Cu—Al alloy at a temperature of 550° C. or higher and 650° C. or lower after the melting and casting step.

The method for producing an alloy in the present invention includes controlling the cooling rate at the time of forming the molten metal into the alloy ingot in the melting and casting step. Accordingly, the cooling rate is increased to suppress occurrence of segregation, so that material structures are homogeneous in a casting process. As a specific condition regarding the cooling rate, the molten metal solidification time is 6.0 sec or less. In cooling with a solidification time of more than 6.0 sec, solidified structures including segregation may be formed. The solidification time can be set in accordance with a relationship of a material of a mold, a composition of an alloy as a cast product and a surface area and a volume of the cast product. A specific method for producing a Au—Cu—Al alloy with the solidification time set to 6.0 sec or less in the present invention, a water-cooled copper mold is employed. The lower limit of the solidification time is preferably 0.3 sec or more in light of apparatus constraints. Preferably, the melting and casting step is carried out in a non-oxidizing atmosphere (vacuum atmosphere, inert gas atmosphere, etc.).

After the melting and casting step, the alloy ingot is subjected to the hot-pressing step. Hot-pressing is performed to ensure that material structures are homogeneous. In the melting and casting step, segregation may occur even when the cooling rate is controlled. In particular, in solidified structures (dendritic structures), very small segregation may occur between trees). In the solidified structures, very small pores (voids) may be formed. In the present invention, solidified structures are destroyed by hot-pressing to eliminate fine segregation, pores and the like so that the material structures are homogeneous.

As a condition for the hot-pressing, a heating temperature is 550° C. or higher and 650° C. or lower. When the heating temperature is lower than 550° C., destruction of solidified structures is insufficient. When the heating temperature is higher than 650° C., crystal grains may be enlarged, resulting in embrittlement. A pressurizing force of the hot-pressing is preferably 50 MPa or more and 150 MPa or less, and a pressing time is preferably 600 sec or more.

Preferably, the hot-pressed alloy is further subjected to homogeneity heat treatment in which heating is performed at a predetermined temperature. Accordingly, the material structures can be made further homogeneous. It is preferable that in the homogeneity heat treatment, the alloy is heated and held at a temperature of 450° C. or higher and 550° C. or lower. A heat treatment time is preferably 3000 sec or more and 4000 sec or less. Preferably, the heat-treated alloy is rapidly cooled (oil-cooled, water-cooled or hot water-cooled).

Advantageous Effects of the Invention

As described above, the superelastic alloy of the present invention is an alloy capable of exhibiting superelasticity at normal temperature while being Ni-free. The superelastic alloy of the present invention has the bulk magnetic susceptibility controlled to fall within an appropriate range, and is artifactless in a magnetic environment. The superelastic alloy including a Au—Cu—Al alloy of the present invention has favorable biocompatibility and a favorable X-ray-imaging property.

Because of many advantages as described above, the present invention can be expected to be applied to various medical devices as a medical material. Specifically, the present invention is applicable to medical devices such as embolization coils, orthodontics tools, clasbs, artificial dental roots, clips, staples, catheters, stents, bone plates and guide wires.

DESCRIPTION OF EMBODIMENTS

Hereinafter, an embodiment of the present invention will be described. In this embodiment, Au—Cu—Al alloys while concentrations of Cu and Al were changed, and various properties such as a superelastic property in a normal temperature range, a bulk magnetic susceptibility, mechanical properties and processability were then evaluated.

For preparation of the superelastic alloy, Cu having a purity of 99.99%, Al having a purity of 99.99% and Au having a purity of 99.99% were used as melt raw materials. By use of a non-consumable W electrode-type argon arc melting furnace, these raw materials were melted in an Ar-1% $H_2$ atmosphere, and a molten metal thus obtained was solidified to produce a Au—Cu—Al alloy ingot. In this embodiment, the molten metal was cast with a water-cooled copper mold, and a solidification time here was 1.6 sec.

Next, the produced alloy ingot was treated by hot-pressing. The hot-pressing was performed by pressing the ingot in vacuum at 600° C. and 100 MPa for 3600 sec. After the hot-pressing treatment, the alloy ingot was heated at 500° C. for 3.6 ksec to make the ingot homogeneous. The ingot (thickness: 1 to 2 mm) subjected to the homogeneity treatment was gradually cooled, and used for preparation of test pieces.

The alloy ingot was subjected to discharge processing to prepare tension test pieces (thickness: 0.2 mm, width: 2 mm and length: 20 mm). Alloys processed into the test pieces were subjected to final heat treatment. The heat treatment was performed by heating the alloy at 500° C. for 1 hour, followed by rapid cooling.

For each test piece, the superelastic property, the bulk magnetic susceptibility, mechanical properties and processability were evaluated. Methods for evaluation of the properties are as follows.

Superelastic Property

A transformation temperature (Ms) was measured by a DSC (differential scanning calorimetry) method. As a heating condition, a temperature elevation or fall rate over a range of −150° C./min to 150° C. was 10° C./min. Test pieces having a measured transformation temperature of 310 K (37° C.) or lower were rated excellent (⊚) because it would be possible to exhibit superelasticity. Test pieces having a transformation temperature of higher than 310 K (37° C.) were rated poor (×).

Bulk Magnetic Susceptibility (Artifact)

A bulk magnetic susceptibility (Xvol) of each test piece was measured by a magnetic balance. The measurement was performed at room temperature. A deviation of the measured bulk magnetic susceptibility from a magnetic susceptibility of water (−9 ppm) was calculated. Test pieces with a deviation within ±5 ppm were rated excellent (⊚), test pieces with a deviation within ±15 ppm or less were rated good (○), and test pieces with a deviation beyond ±15 ppm were rated poor (×).

Mechanical Properties

For each test piece, a Vickers hardness (HV) was measured with a Vickers tester (load: 300 gf). For evaluation, test pieces having a Vickers hardness of 300 Hv or more were rated excellent (⊚), test pieces having a Vickers hardness of 200 Hv or more were rated good (○), test pieces having a Vickers hardness of 150 Hv or more were rated fair (Δ), and test pieces having a Vickers hardness of less than 150 Hv were rated poor (×).

Processability

For each test piece, a compression strain (ε) was measured with a compression tester. The measurement was performed at room temperature and a strain rate of $3.3 \times 10^{-4}$ $s^{-1}$. For evaluation, test pieces having a compression strain (ε) of 10% or more were rated excellent (⊚), test pieces having a compression strain (ε) of 5% or more were rated good (○), and test pieces having a compression strain (ε) of less than 5% were rated poor (×).

The measurement results and evaluation results of the above properties are shown in Table 1.

TABLE 1

| | Composition (at %) | | | Superelastic property | | Bulk magnetic susceptibility (artifact) | | Mechanical property | | Processability | |
|---|---|---|---|---|---|---|---|---|---|---|---|
| No. | Au | Cu | Al | Ms/K | Evaluation | Xvol/ppm | Evaluation | HV/Hv | Evaluation | ε/% | Evaluation |
| 1 | Balance | 27.0 | 18.0 | 266 | ⊚ | −3.5 | ○ | 232 | ○ | 9.6 | ○ |
| 2 | | 28.0 | 22.0 | 291 | ⊚ | −0.6 | ○ | 152 | Δ | 18.2 | ⊚ |
| 3 | | 25.0 | 25.0 | 294 | ⊚ | −2.7 | ○ | 166 | Δ | 14.0 | ⊚ |

TABLE 1-continued

| | Composition (at %) | | | Superelastic property | | Bulk magnetic susceptibility (artifact) | | Mechanical property | | Processability | |
|---|---|---|---|---|---|---|---|---|---|---|---|
| No. | Au | Cu | Al | Ms/K | Evaluation | Xvol/ppm | Evaluation | HV/Hv | Evaluation | ε/% | Evaluation |
| 4 | | 30.0 | 25.0 | 291 | ◎ | −1.6 | ○ | 249 | ○ | 12.5 | ◎ |
| 5 | | 35.0 | 25.0 | 297 | ◎ | −1.8 | ○ | 381 | ◎ | 7.6 | ○ |
| 6 | | 31.3 | 28.0 | 274 | ◎ | −8.1 | ○ | 398 | ◎ | 2.7 | X |
| 7 | | 45.0 | 25.0 | — | — | 7.0 | X | 142 | X | 9.5 | ○ |

Table 1 reveals that Au—Cu—Al alloys containing Cu in an amount of 20 atom % or more and 40 atom % or less and Al in an amount of 15 atom % or more and 25 atom % or less (No. 1 to No. 5) had a favorable transformation temperature (Ms) and bulk magnetic susceptibility (Xvol), and were capable of attaining exhibition of superelasticity and an artifactless property. These Au—Cu—Al alloys had acceptable mechanical properties (hardness) and processability (compression strain).

On the other hand, an alloy containing Al in an amount of more than 25% (No. 6) had an extremely favorable magnetic susceptibility value owing to the magnetic susceptibility adjustment effect of Al, but significantly poor processability (compression strain). The present invention is based on an assumption that alloys are used as medical materials and processed into medical devices having various shapes, and therefore processability is also an important property. Accordingly, the alloy has unfavorable properties overall. An alloy containing Cu in an amount of more than 40% (No. 7) was confirmed to be an unfavorable alloy because the alloy did not exhibit superelasticity, and had a magnetic susceptibility of more than 6 ppm.

INDUSTRIAL APPLICABILITY

The superelastic alloy of the present invention is an alloy which exhibits superelasticity in a normal temperature range, has an appropriate bulk magnetic susceptibility, and can be artifactless in a magnetic field environment such as MRI. The alloy is free from Ni, and therefore has biocompatibility which is an essential condition as a medical material. The alloy also has a favorable X-ray-imaging property. The present invention can be expected to be applied to various medical devices.

The invention claimed is:

1. An artifactless superelastic alloy comprising a Au—Cu—Al alloy,
    the superelastic alloy containing Cu in an amount of 20 atom % or more and 40 atom % or less, Al in an amount of 15 atom % or more and 25 atom % or less, and Au as a balance,
    the superelastic alloy having a bulk magnetic susceptibility of −24 ppm or more and 6 ppm or less.

2. The superelastic alloy according to claim 1, comprising Cu in an amount of 25 atom % or more and 35 atom % or less, Al in an amount of 18 atom % or more and 25 atom % or less, and Au as a balance.

3. The superelastic alloy according to claim 2, having the bulk magnetic susceptibility of −8.1 ppm or more and −0.6 ppm or less.

4. A method for producing the superelastic alloy defined in claim 1, comprising the steps of:
    melting and casting a Au—Cu—Al alloy containing Cu in an amount of 20 atom % or more and 40 atom % or less, Al in an amount of 15 atom % or more and 25 atom % or less, and Au as a balance,
    the melting and casting step including producing the Au—Cu—Al alloy with a molten metal solidification time set to 6.0 sec or less; and
    hot-pressing the Au—Cu—Al alloy subjected to the melting and casting step at a temperature of 550° C. or higher and 650° C. or lower.

5. The method for producing the superelastic alloy according to claim 4, comprising a homogeneity heat treatment step of heating the alloy after the hot-pressing step at a temperature of 450° C. or higher and 550° C. or lower.

6. A method for producing the superelastic alloy defined in claim 2, comprising the steps of:
    melting and casting a Au—Cu—Al alloy containing Cu in an amount of 20 atom % or more and 40 atom % or less, Al in an amount of 15 atom % or more and 25 atom % or less, and Au as a balance,
    the melting and casting step including producing the Au—Cu—Al alloy with a molten metal solidification time set to 6.0 sec or less; and
    hot-pressing the Au—Cu—Al alloy subjected to the melting and casting step at a temperature of 550° C. or higher and 650° C. or lower.

* * * * *